United States Patent
Hogan

Patent Number: 5,823,432
Date of Patent: Oct. 20, 1998

[54] AIR FRESHNER DEVICE

[76] Inventor: Howard D. Hogan, 603 Province Town, Auburn Hills, Mich. 48326

[21] Appl. No.: 686,318

[22] Filed: Jul. 25, 1996

[51] Int. Cl.$^6$ ..................................................... A24F 25/00
[52] U.S. Cl. ................................ 239/36; 2/406; 450/102; 239/34
[58] Field of Search ................................ 239/34, 36, 57, 239/60; 2/53–57, 406, 170; 450/102–4; 223/86; D23/366–369

[56] References Cited

U.S. PATENT DOCUMENTS

| | | | |
|---|---|---|---|
| D. 303,833 | 10/1989 | Spector | D23/386 |
| D. 346,018 | 4/1994 | Kawakami | D23/367 |
| D. 347,055 | 5/1994 | Jarvis | D23/366 |
| D. 349,762 | 8/1994 | El-Assir | D23/367 |
| D. 353,501 | 12/1994 | Kral | D6/513 |
| D. 359,347 | 6/1995 | El-Assir | D23/367 |
| D. 359,348 | 6/1995 | El-Assir | D23/367 |
| D. 362,495 | 9/1995 | El-Assir | D23/367 |
| D. 362,497 | 9/1995 | Clayton | D23/367 |
| 1,839,073 | 12/1931 | Wright | 239/34 |
| 2,092,728 | 9/1937 | Dearling | 239/34 |
| 2,283,028 | 5/1942 | Bailey | 239/34 |
| 2,719,976 | 10/1955 | Sussman | 450/103 |
| 3,065,915 | 11/1962 | Samann | 239/35 |
| 3,152,762 | 10/1964 | Englehart | 239/45 |
| 3,698,991 | 10/1972 | Susewitz | 161/14 |
| 4,285,905 | 8/1981 | Feit | 422/4 |
| 4,419,395 | 12/1983 | Sugimoto | 428/28 |
| 4,465,232 | 8/1984 | Field | 239/36 |
| 4,476,171 | 10/1984 | Takeuchi | 428/38 |
| 4,535,935 | 8/1985 | Spector | 239/34 |
| 4,678,206 | 7/1987 | Leahan | 281/158 |
| 4,708,851 | 11/1987 | Von Loringhoven | 422/123 |
| 4,744,514 | 5/1988 | Gadoua | 239/36 |
| 4,860,953 | 8/1989 | Hsien | 239/47 |
| 4,883,692 | 11/1989 | Spector | 428/16 |
| 4,957,787 | 9/1990 | Reinhardt et al. | 428/24 |
| 5,004,138 | 4/1991 | Gabas | 224/312 |
| 5,037,343 | 8/1991 | Benites | 446/268 |
| 5,093,935 | 3/1992 | Countes, Jr. | 2/400 |
| 5,172,430 | 12/1992 | Lerman-Solis | 2/400 |
| 5,172,863 | 12/1992 | Melone et al. | 239/211 |
| 5,197,639 | 3/1993 | Jerman et al. | 223/88 |
| 5,282,571 | 2/1994 | Smith et al. | 239/54 |
| 5,383,598 | 1/1995 | Styles | 239/57 |
| 5,407,642 | 4/1995 | Lord | 422/122 |
| 5,423,711 | 6/1995 | Dorland | 450/57 |
| 5,478,505 | 12/1995 | McElfresh et al. | 261/30 |

*Primary Examiner*—Andres Kashnikow
*Assistant Examiner*—Lisa Ann Douglas
*Attorney, Agent, or Firm*—Harness, Dickey and Pierce, P.L.C.

[57] ABSTRACT

An air freshener device in which an insert provides shape to article of clothing so that the air freshener device assumes the shape of the article of clothing. The insert preferably formed so that assembly of the air freshener device inherently shapes the article of clothing. The air freshener device also includes a pouch formed in the article of clothing to receive scented beads or other aromatic material. The pouch and the air freshener device provides air flow over the scented material so that the scented material properly disseminates the scent in order to freshen the environment.

16 Claims, 1 Drawing Sheet

AIR FRESHNER DEVICE

BACKGROUND OF THE INVENTION

1. Technical Field

This invention relates generally to an air freshener device, and more particularly, to an air freshener device formed in the shape of an article of clothing and having a frame or insert integrally assembled with the air freshener device in order to impart to and maintain a desired shape of the article of clothing.

2. Discussion

In boats, cars, houses, and other spaces having a closed environment with limited air exchange properties, the air often becomes stale and acquires an undesirable odor. There are many products known in the art which can be placed in such environments in order to improve the air quality by emitting a more desirable odor or scent. Such devices, however, often provide unsightly appearances and must be placed in a less centralized, less visible location in order to minimize detracting from the appearance of the environment.

For example, in automobiles, various air fresheners adhere to various locations of the automobile. However, as stated above, these air fresheners detract from the decorative appearance of the vehicle. Consequently, the air fresheners are placed toward the underside of the dashboard or some other location low in the vehicle interior. Such placement, while hiding the unsightly air freshener, often inhibits dispersion spread of the aroma from the air freshener because the air freshener is placed in a relatively poorly ventilated area.

Therefore, it is an object of the present invention to provide an air freshener device for a vehicle, boat, or home which may be placed in a central location in order to maximize emission of the desired scent.

It is a further object of the present invention to provide an air freshener device having a decorative appearance which does not detract from the overall appearance of the environment in which it is placed.

It is yet a further object of the present invention to provide an air freshener device which may be placed in a centralized location in an automobile to facilitate dispersion of the scent throughout the automobile.

SUMMARY OF THE INVENTION

The invention described herein satisfies all of the foregoing needs. Accordingly, the present invention describes an air freshener device, including an article of clothing. A ventilated pouch is formed in the article of clothing, and a scented material is inserted into the ventilated pouch so that the article of clothing emits the scent of the scented material from the ventilated pouch. A frame for provides shape to the article of clothing and is assembled integrally with the article of clothing. The frame also includes an attachment means for hanging the frame. From the subsequent detailed description taken in conjunction with the accompanying drawings and subjoined claims, other objects and advantages of the present invention will become apparent to those skilled in the art.

DETAILED DESCRIPTION OF THE PREFERRED EMBODIMENTS

Figure 1:
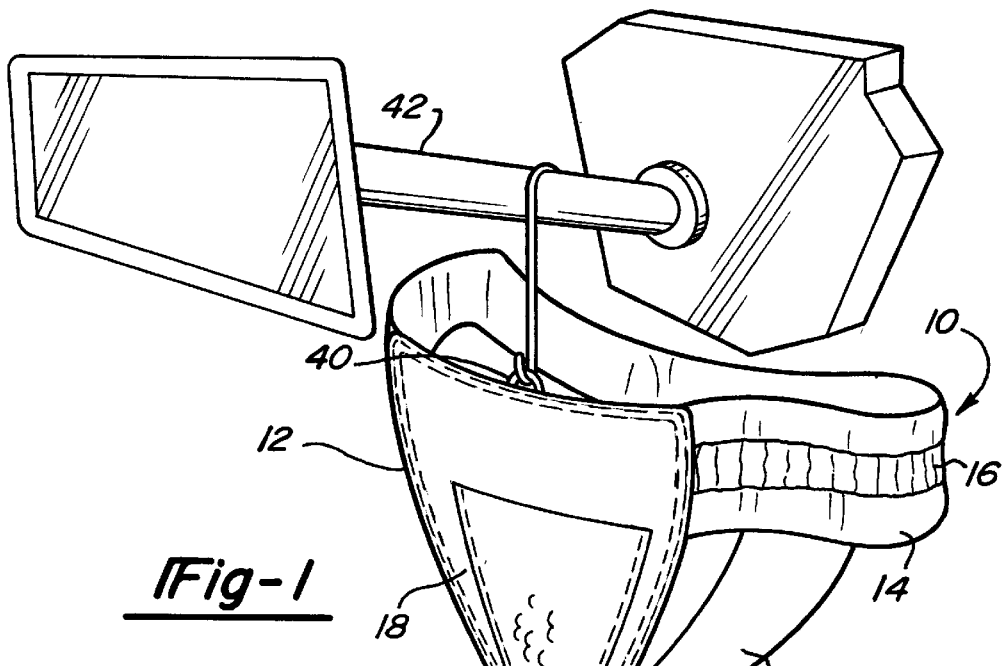
FIG. 1 is a perspective of the air freshener device arranged in accordance with the principles of the present invention.
Figure 2:
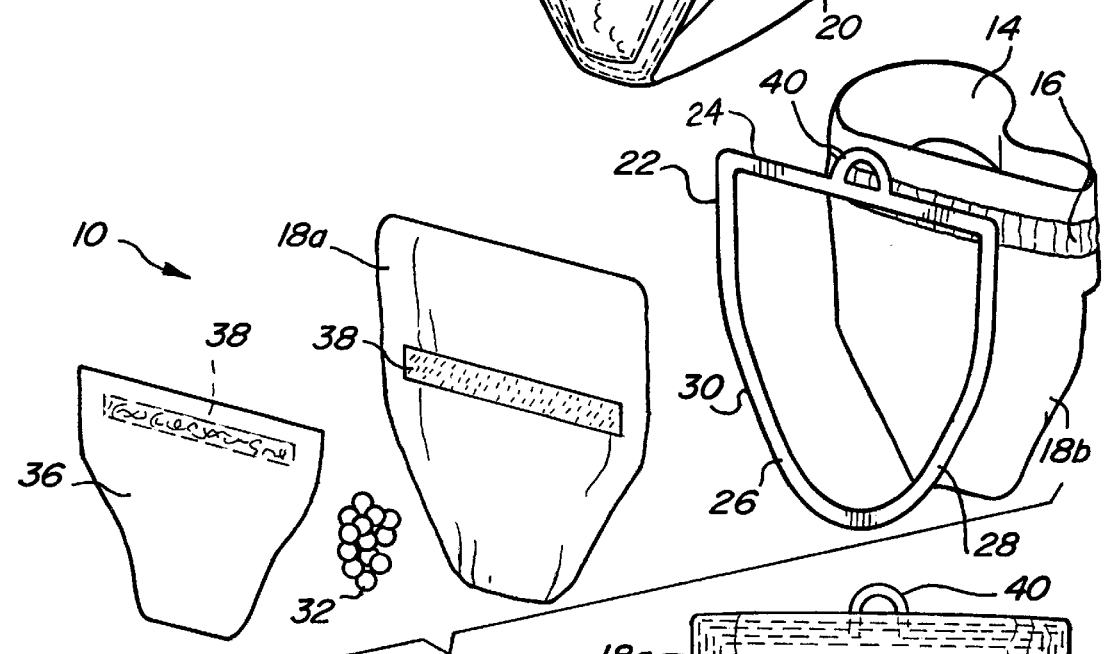
FIG. 2 is an exploded view of the air freshener device showing the component parts which comprise the device.
Figure 3:
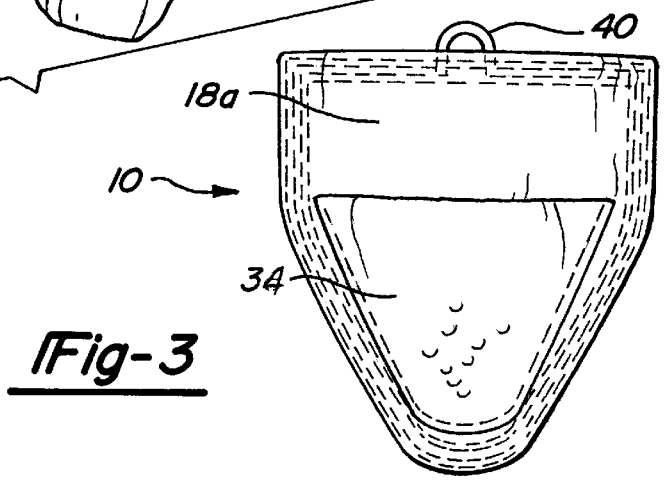
FIG. 3 is a front elevational view of the air freshener device of FIG. 1.

FIG. 1 depicts the air freshener device 10 arranged in accordance with the principles of the present invention. The air freshener device 10 includes a miniature article of clothing or garment 12, which may be any of a number of clothing articles or garments known to those skilled in the art and which may be supported in accordance with the teachings herein. In particular, the garment 12 in FIGS. 1–3 is depicted as a pant undergarment. The garment 12 incudes a generally circular waistband 14 having a elastic 16 sewn into the waistband 14 to provide stretch to the waistband 14. A front section 18 descends from the waistband 14 and generally corresponds to the front section of a typical pant undergarment. The lower portion of the front section 18 is interconnected to a rear portion of the waistband 14 by a band of material 20. The band of material 20 is typically sewn to both the waistband 14 and a predetermined area of the lower portion of the front section 18.

Without support, the garment 12 would merely hang downward with minimal shape. One particular feature of this invention is the incorporation of an insert 22 incorporated into the front section 18 in order to provide shape to the garment 12. The insert 22 typically includes a plastic frame having an upper section 24, a lower section 26, a left side section 28, and a right side section 30. Each of the four sections 24–30 are interconnected to form a shape as shown by insert 22. The insert 22 is typically assembled into the front section 18 of the garment 12.

For example, the front section 18 may include a front panel 18a and a rear panel 18b. The insert 22 is typically interposed between the front and rear panels 18a, 18b and then stitched or glued in place in accordance with the particular design choices during assembly. Insert 22 is typically sized larger than the front section 18. When the insert 22 is oversized, the insert 22 assumes an arcuate or rounded shape when sewn or glued between the front and rear panels 18a, 18b of front section 18. By oversizing the insert 22, the insert 22 arcs in a shape which provides a realistic shape to the garment 12.

A plurality of air freshener beads 32 or singular air freshener device are inserted into a pouch 34 attached to the front panel 18a of front section 18. The pouch may be formed by providing an additional panel of material 36 onto the front panel 18a. The panel 36 may be stitched to the front section 18. The pouch 34 preferably includes a closure device 38 such as velcro or a zipper so that the air freshener beads 32 may be replaced as necessary. Further, one skilled in the art will understand that the front section 18 and pouch 34 are preferably air permeable so that the aroma of the air freshener beads 32 may escape from within the pouch in order to provide air freshener capability.

The insert 22 also includes a suspension mechanism 40 so that the air freshener device 10 may be hung from a rear view mirror 42 of an automobile, for example, or other instrument for suspending the air freshener device.

It will be understood by one skilled in the art that while the air freshener device 10 was described in the context of a pant undergarment, various other pant garments may be substituted and given shape by an insert suitably adapted. Further, it will be understood by one skilled in the art that the insert is preferably formed of plastic so that the insert 22 deforms relatively easily when assembled in order to provide the preferred shape to the air freshener device 10.

Although the invention has been described with particular reference to certain preferred embodiments thereof, variations and modifications can be effected within the spirit and scope of the following claims.

What is claimed is:

1. An air freshener device, comprising:

an article of clothing;

a ventilated pouch formed in the article of clothing;

a scented material inserted into the ventilated pouch, the article of clothing emitting the scent of the scented material from the ventilated pouch;

a frame for providing shape to the article of clothing, the frame being assembled integrally with the article of clothing; and an attachment means for hanging the frame.

2. The air freshener device of claim 1 wherein the frame is arcuately shaped to support the article of clothing to maintain a desired shape in the article of clothing.

3. The air freshener device of claim 1 wherein the attachment means comprises an ear attached to the frame.

4. The air freshener device of claim 3 wherein the ear receives a means for hanging the frame.

5. The air freshener device of claim 4 wherein the means for hanging attaches to the mirror of a car.

6. The air freshener device of claim 1 wherein the frame further includes a lip for receiving an elastic portion of the article of clothing.

7. The air freshener device of claim 1 wherein the frame is integrally attached to the article of clothing by stitching the article of clothing to the frame.

8. An air freshener device, comprising:

a pant undergarment;

a ventilated pouch formed in the pant undergarment;

a scented material inserted into the ventilated pouch, the pant undergarment emitting the scent of the scented material from the ventilated pouch;

an insert for providing shape to the pant undergarment, the insert being assembled integrally with the pant undergarment; and a means for attachment extending from the insert for hanging the insert.

9. The air freshener device of claim 8 wherein the insert is arcuately shaped to support to the pant undergarment a desired shape for the pant undergarment.

10. The air freshener device of claim 8 wherein the attachment means attaches to a means for hanging the frame.

11. The air freshener device of claim 10 wherein the means for hanging attaches to the rear-view mirror of the car.

12. The air freshener device of claim 8 wherein the insert further comprises:

a narrow lower section;

a pair of lower legs having first ends connecting to and extending from the lower section, the lower legs, bending upward and outward from the lower section;

a pair of upper legs having first ends connected to and extending generally upward from the second ends of the lower legs; and an upper section between the second ends of the upper legs, the upper section forming an upper lip of the insert.

13. The air freshener device of claim 12 wherein the upper section forms an arc between the upper legs, providing an arcuate shape to the insert in the direction of the upper section.

14. The air freshener device of claim 13 wherein the lower legs form and arc between the upper and lower sections, providing an arcuate shape to the insert in the direction of lower legs.

15. The air freshener device of claim 12 wherein the lower legs form and arc between the upper and lower sections, providing an arcuate shape to the insert in the direction of lower legs.

16. The air freshener device of claim 8 wherein the undergarment pant is sewn together and the insert is integrally assembled with the undergarment pant by sewing the insert into the undergarment pant.

* * * * *

UNITED STATES PATENT AND TRADEMARK OFFICE
CERTIFICATE OF CORRECTION

PATENT NO. : 5,823,432
DATED : October 20, 1998
INVENTOR(S) : Howard D. Hogan

It is certified that error appears in the above-identified patent and that said Letters Patent is hereby corrected as shown below:

ON THE TITLE PAGE, "FRESHNER" should be --FRESHENER--.

Signed and Sealed this

Twenty-third Day of May, 2000

Attest:

Q. TODD DICKINSON

*Attesting Officer*   *Director of Patents and Trademarks*